(12) United States Patent
Bouvier

(10) Patent No.: US 9,089,309 B2
(45) Date of Patent: Jul. 28, 2015

(54) MULTIPLANE MEDICAL IMAGING SYSTEM

(75) Inventor: Bernard Bouvier, Eragny sur Oise (FR)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 248 days.

(21) Appl. No.: 13/423,998

(22) Filed: Mar. 19, 2012

(65) Prior Publication Data

US 2012/0328077 A1 Dec. 27, 2012

(30) Foreign Application Priority Data

Mar. 24, 2011 (FR) ...................... 11 52457

(51) Int. Cl.
*A61B 6/00* (2006.01)

(52) U.S. Cl.
CPC ............... *A61B 6/547* (2013.01); *A61B 6/4014* (2013.01); *A61B 6/4458* (2013.01); *A61B 6/4464* (2013.01); *A61B 6/4476* (2013.01); *A61B 6/504* (2013.01); *A61B 6/5223* (2013.01)

(58) Field of Classification Search
CPC .. A61B 6/4014; A61B 6/4405; A61B 6/4458; A61B 6/4464; A61B 6/4476; A61B 6/547
USPC .................. 378/196, 197, 198, 117
See application file for complete search history.

(56) References Cited

U.S. PATENT DOCUMENTS

| 4,426,725 | A | | 1/1984 | Grady |
| 5,479,470 | A | * | 12/1995 | Stenfors ........................ 378/197 |
| 6,120,180 | A | | 9/2000 | Graumann |
| 6,435,713 | B1 | * | 8/2002 | Iizuka ........................... 378/197 |
| 2004/0170255 | A1 | | 9/2004 | Akutsu et al. |
| 2005/0195945 | A1 | | 9/2005 | Gotoh |
| 2009/0028290 | A1 | | 1/2009 | Grebner et al. |
| 2010/0296632 | A1 | * | 11/2010 | Bouvier ........................ 378/198 |

OTHER PUBLICATIONS

Search Report from corresponding FR application No. 1152457, date as Aug. 25, 2011.
Unofficial translation of Chinese Search Report from CN Application No. 201210097636.3 dated Dec. 5, 2014.

* cited by examiner

*Primary Examiner* — Glen Kao
(74) *Attorney, Agent, or Firm* — GE Global Patent Operation; Marc A. Vivenzio

(57) ABSTRACT

A multiplane medical imaging system is provided. The multiplane medical imaging system comprises a first X-ray machine and a second X-ray machine, each X-ray machine comprising an X-ray tube and an X-ray detector, wherein the first and second X-ray machines each comprise respective mobile automatic devices on which the respective X-ray tubes and the respective X-ray detectors are mounted in order to control the movement of the first and second X-ray machines.

12 Claims, 4 Drawing Sheets

MULTIPLANE MEDICAL IMAGING SYSTEM

BACKGROUND OF THE INVENTION

1. Field of the Invention

Embodiments of the invention relate to medical imaging systems and, more particularly, to multiplane medical imaging systems capable of producing radiographic images in several planes and allowing the examination of an area of interest in several planes.

2. Description of Related Art

Imaging systems usually comprise an X-ray machine comprising an X-ray tube and an X-ray detector placed opposite the X-ray tube in the direction of emission of X-rays. The tube and the detector are usually placed on two mutually opposite ends of an arm.

Such systems are used for angiographic examinations for diagnostic or interventional purposes. During these examinations, it is necessary to produce radiographs by X-rays of an area of interest in the body of a patient. For this purpose, after the patient has been laid out on an examination table, the X-ray tube and the detector are brought to face the area to be radiographed.

A known X-ray system that is fixed to the floor comprises an arm that supports the X-ray tube and the detector, the arm comprising several degrees of freedom that makes it possible to position the X-ray beam facing an area of interest.

This type of system, however, has a major drawback relating to the fact that the radiography need is only necessary during a limited time of the procedure. Meanwhile, access to the patient must be given priority. The systems can therefore not be moved away from the examination table when they are not in use. In particular, the transfer and the placement of the patient on the examination table are hampered by the presence of this cumbersome system. It has therefore been proposed to mount the X-ray machine on a mobile device mounted on wheels driven by motors controlled automatically under the control of a navigation system.

There are also X-ray systems called "surgical mobile" units that can be moved manually. These systems are mounted on a carriage that contains batteries used to supply the X-ray tube with power. This type of system is not suitable for angiographic examinations because the power delivered by the X-ray tube is not sufficient to obtain adequate image quality and, in particular, adequate contrast.

Moreover, this type of mobile X-ray system does not allow complex angulations because the diameter of the arm supporting the tube and the detector is not big enough. Similarly, these mobile X-ray systems do not achieve sufficient rotation speeds to allow good quality, three-dimensional image reconstructions. Finally, even though the weight of such a system is half as much as that of an X-ray machine designed for angiography, it remains very difficult to move because of its relatively large dimensions and weight, which can be up to about 300 kg (about 660 lbs).

Finally, X-ray systems for angiography that are suspended from the ceiling and can be moved on guiderails via a mobile carriage driven, for example, with the aid of an electric motor, are known.

During the implementation of angiographic examinations, it may be necessary to use multiplane medical imaging systems, for example biplane systems, that are capable of forming images of a vessel in several planes in order to visualize the vessels in these different planes, most frequently perpendicular planes.

Biplane medical imaging systems, therefore, comprise two X-ray machines each capable of forming an image in one plane. These machines are, for example, mounted either on the floor or on the ceiling.

A multiplane medical imaging system has been described which comprises, for example, a first X-ray machine mounted on a robot fixed to the floor, and a second X-ray machine supported by a second robot that can move relative to the floor or is mounted to slide on rails attached to the ceiling.

In this type of medical imaging system, the X-ray machines are relatively bulky so that, during the radiological examination, access to the patient on an examination table is considerably limited.

This access limitation is due to the location of the first X-ray machine. Being fixed to the floor in the vicinity of the frontal zone of an examination or operating table on which the patient is located, considerably limits access to the patient.

Moreover, the radiographic requirements for certain examinations or interventions are necessary only for a limited period of the procedure. Meanwhile, it is access to the patient or to the examination table that must be given priority, so it is desirable that the X-ray machines are both moved away from the table, for example, during the transfer and the positioning of the patient on the table.

Finally, in certain types of examination for interventional purposes, it may be essential to keep the examination table, itself mobile, in a fixed position in order to prevent moving the patient. In such a configuration, the X-ray machines of the multiplane imaging system are the only items to be moved and brought to face the area of interest to be radiographed. Here again, fixing the robot to the floor is likely to limit the ability to move the X-ray machine.

In view of the foregoing, there exists a need to have a multiplane medical imaging system and, notably, a biplane system that is capable of increasing the degrees of freedom of the X-ray machines by increasing their ability for movement.

BRIEF DESCRIPTION OF THE INVENTION

According to an embodiment of the present invention, a multiplane medical imaging system is provided. The multiplane medical imaging system comprises a first X-ray machine and a second X-ray machine each comprising an X-ray tube and an X-ray detector, wherein the first and second X-ray machines each comprise respective mobile automatic devices on which the respective X-ray tubes and the respective X-ray detectors are mounted in order to control the movement of the first and second. X-ray machines.

According to another embodiment of the present invention, a method for moving a multiplane medical imaging system, the system comprising a first X-ray machine and a second X-ray machine each comprising an X-ray tube and an X-ray detector, wherein the first and second X-ray machines each comprise respective mobile automatic devices on which the respective X-ray tubes and the respective X-ray detectors are mounted in order to control the movement of the first and second X-ray machines. The method comprises acquiring information relating to the position of the first and second X-ray machines, and controlling the movement of mobile automatic devices according to the information relating to the position of the first and second X-ray machines.

BRIEF DESCRIPTION OF THE DRAWINGS

Other objects, features and advantages of the embodiments of the present invention will appear on reading the following description, given only as a non-limiting example, and made with reference to the appended drawings in which.

DETAILED DESCRIPTION OF THE INVENTION

Figure 1:
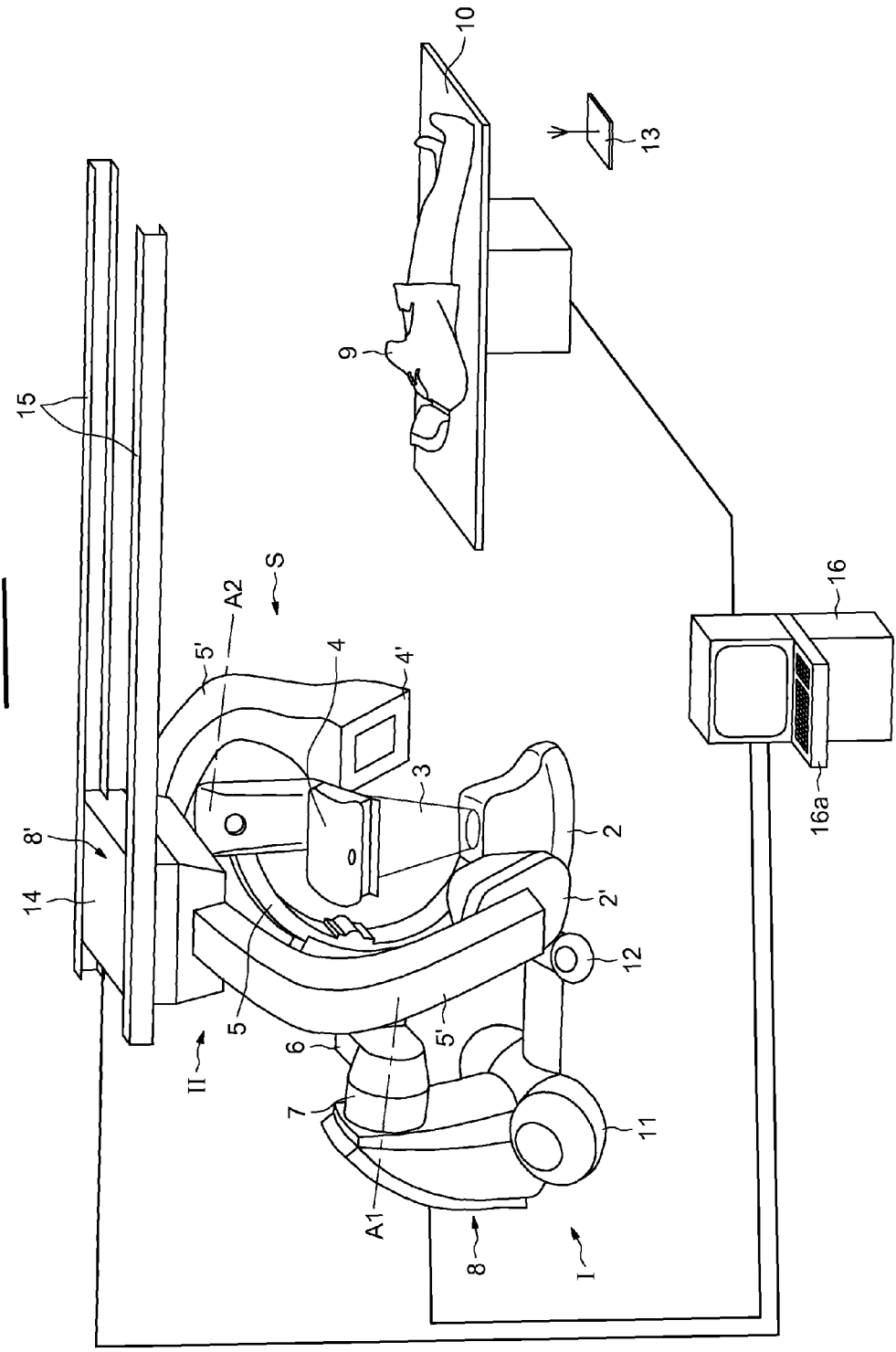
FIG. 1 is a schematic view of a biplane X-ray system in the out-of-the-way waiting position according to an embodiment of the present invention.

FIG. 1 illustrates a vascular biplane medical imaging system. The imaging system may be used for an angiographic examination and is especially designed to provide views on two different planes of a vessel in order to view them in these two planes, which in this instance, are perpendicular.

The imaging system S is equipped with two X-ray machines I, II, each ensuring a view in one plane.

These two machines I, II, are each mounted on a mobile robotic device and are each capable of moving according to the examination phases. The first X-ray machine I can be moved on the floor, while the second machine II can be moved on the ceiling of an examination or operating room.

The first machine I comprises an X-ray tube 2, capable of emitting a beam 3 of X-rays in an emission direction, and an X-ray detector 4 placed at the two mutually opposite ends of an arm 5, in this instance in the form of an arch, so that the X-rays emitted by the tube 2 are incident to the detector 4.

As shown, the arm 5 is mounted slidingly on a second, rotary arm 6 mounted so as to rotate on a fixed support 7, itself mounted on a mobile device 8. Therefore, the support 7, the rotary arm 6 and the arm 5 are all articulated relative to one another about articulation axes, such as A1, so that the X-ray machine can be moved in three dimensions and thus take images of an organ to be examined at various angles of incidence.

During radiography, the tube 2 and the detector 4 are brought to face an area of interest in the body 9 of a patient lying on an examination table 10 so that, when the area of interest is interposed between the X-ray tube 2 and the detector 4, it is irradiated by the X-rays, and the detector 4 produces representative data of features of the interposed area of interest.

Mobile device 8 includes, in an exemplary embodiment, a running system comprising, for example, two lateral drive and steering wheels 11 placed at the rear, two free front wheels 12, and means for driving the drive wheels comprising a steering motor coupled to a drive motor. The mobile device 8 is a programmable robotic device and is associated with a navigation system capable, for example, of communicating by radio link identification devices 13 placed in the operating room in order to allow the machine I to locate itself precisely in the room and, in particular, relative to the examination table 10.

The second X-ray machine II also comprises an X-ray tube 2' and an X-ray detector 4' placed opposite to the X-ray tube 2'. The X-ray tube 2' and the detector 4' are each mounted on an articulated arm 5', the arms themselves each being mounted on a mobile robotic device 8'. These arms are articulated about several articulation axes, such as A2, thus making it possible to adjust the position of the X-ray tube 2' and of the detector 4' in three dimensions relative to an area of interest.

The mobile device 8' comprises a support 14 provided with drive means and mounted slidingly on parallel longitudinal rails 15, themselves attached to the ceiling of the examination or operating room and having a first end positioned away from the examination table 10, corresponding to a parking position for the machine II and an opposite end situated facing the examination table 10, corresponding to an active position of the machine II.

The drive means for support 14 are, for example, rollers driven by a drive motor on board the support 14 or in the form of belts capable of moving the support 14 depending on the examination phases. Specifically, during radiography, the tube 2' and the detector 4' are brought to face an area of interest in the body 9 of the patient.

Figure 2:
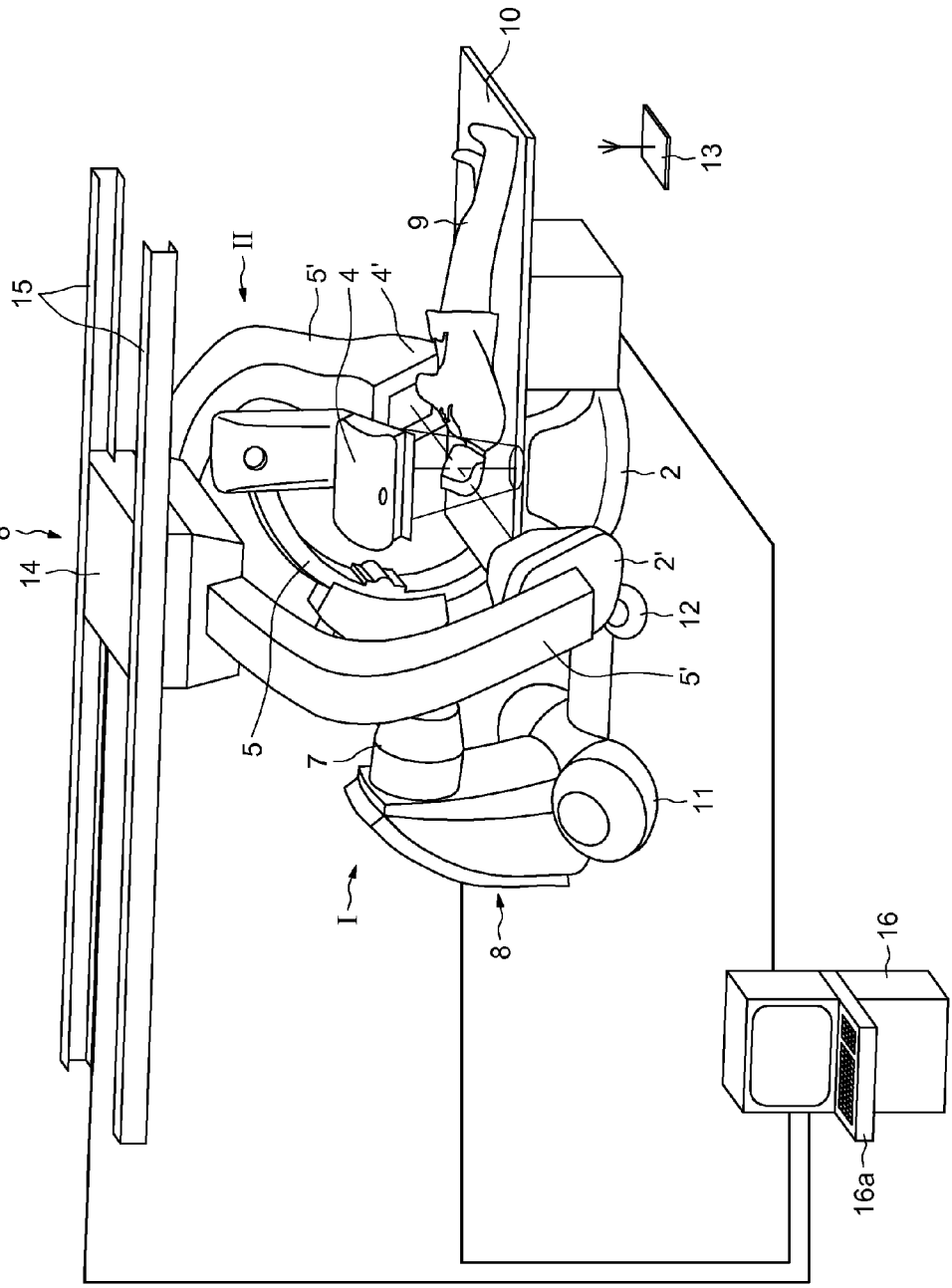
FIG. 2 shows the system of FIG. 1 during an examination according to an embodiment of the present invention.
Figure 3:
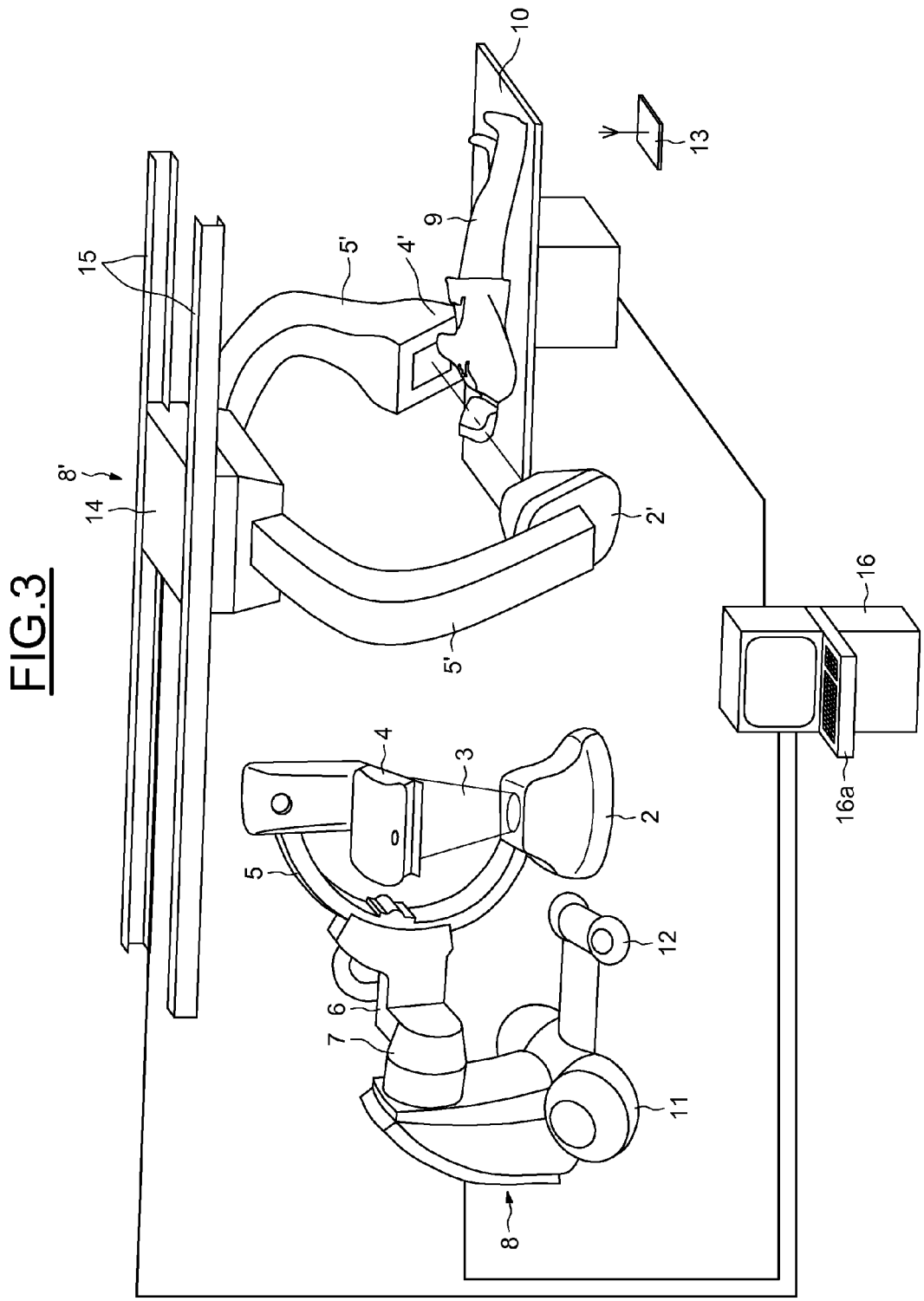
FIG. 3 shows the system of FIGS. 1 and 2 during the taking of a monoplane view according to an embodiment of the present invention.

It is also possible to see in FIGS. 1-3 that the system S, and in particular the two X-ray machines I, II, are connected to a common central processing unit 16, schematically represented, that is furnished with a control console 16a and duly programmed to control the movement of the two machines I, II depending on the phases of an examination to be conducted.

In particular, the central processing unit 16 is furnished with storage means, of the data storage memory type, of the ROM, RAM, etc. type, incorporating one or more control algorithms capable of moving the X-ray machines I, II either automatically, or under the control of the control console 16a, under the action of instructions entered manually by an operator.

As will be specified below, the central processing unit 16 also manages the movements of the machines I, II relative to the table 10. In one embodiment, the central processing unit 16 also incorporates one or more navigation algorithms, stored in memory, in order to locate the machines I, II based on location information generated by detectors provided on the machines I, II in order to communicate with the identification devices 13.

Outside examination phases, the central processing unit 16 controls the driving means of the mobile device 8 of the first X-ray machine I and of the mobile device 8' of the second X-ray machine II to position the two machines I, II in an out-of-the-way position (FIG. 1) in order to clear the examination table 10 during the transfer and positioning of the patient on the examination table 10. This may also be the case, during an intervention that does not require radiological examination. This out-of-the-way position may correspond to a predetermined position stored in the memory of the central processing unit 16 or to a control instruction entered by an operator by means of the console 16a.

As shown in FIG. 2, during a radiographic examination, the central processing unit 16 controls, either automatically, or under the control of the console 16a, the movement of the two X-ray machines I, II so as to bring the X-ray tubes 2, 2' and the detectors 4, 4' to face the area of interest to be radiographed. The movement of the machines I, II involves the implementation of the mobile devices 8 and 8' and the articulation of the arms 5, 5' in order to position the tubes 2, 2' and the detectors 4, 4' to face the area of interest. During this phase, the isocentre of the axes of the two machines I, II, namely the meeting points of the X-rays emitted and received by each of the machines, can be moved along the axis of the table 10 without the patient having to be moved.

Moreover, during the radiographic examination, the first machine I on the floor can be brought into various locations in an examination room, around the examination table 10, while controlling the positioning of the X-ray tube 2 and of the detector 4 in order to position them to face an area of interest. The positions to which the machines I, II can be moved can be either positions programmed in memory in the central processing unit 16 or correspond to control instructions entered by the operator.

Figure 4:
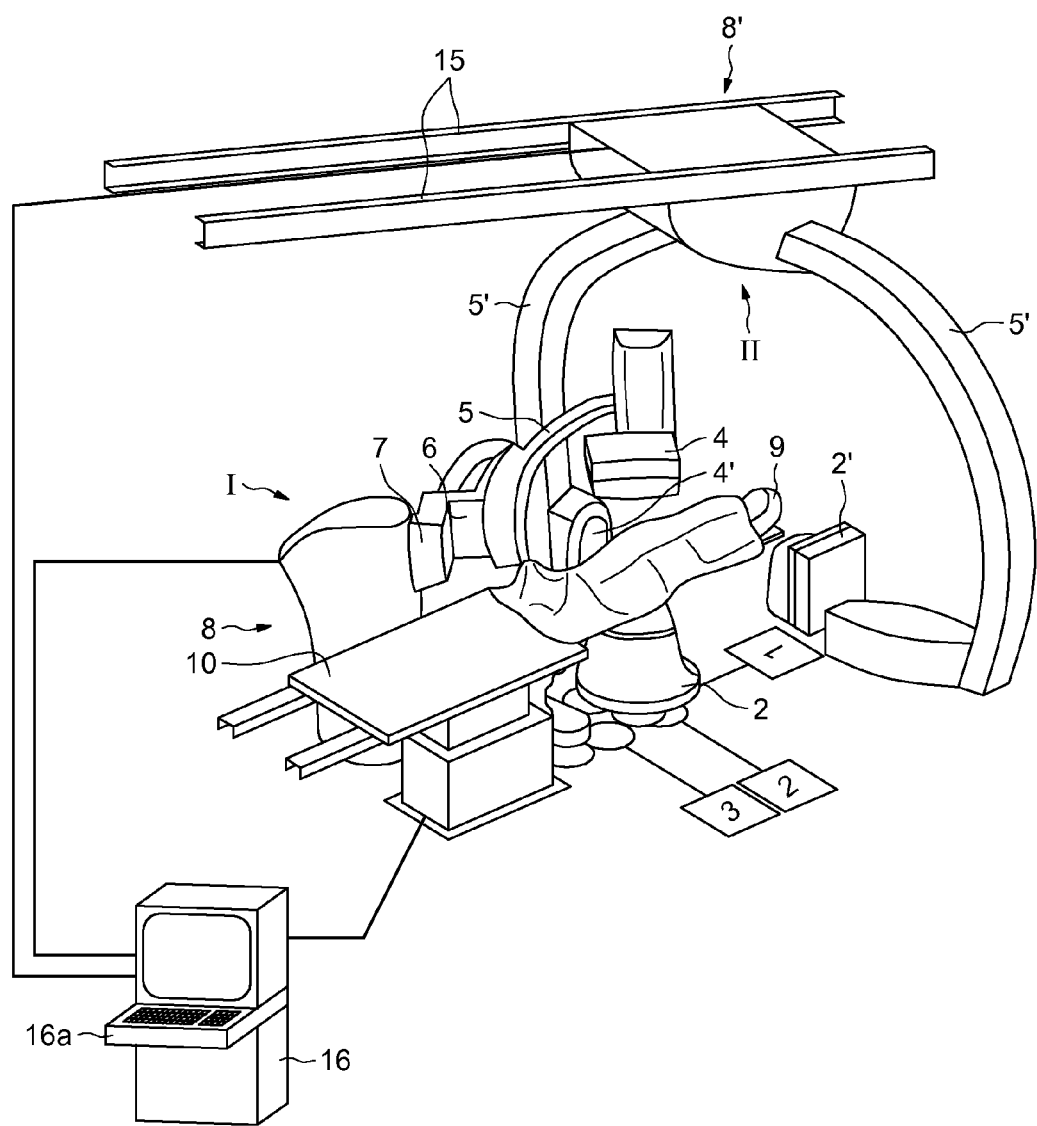
FIG. 4 shows the system of FIGS. 1 and 2 during the taking of a biplane view and in a configuration in which one of the X-ray machines is positioned on one side of an examination table according to an embodiment of the present invention.

For example, as shown in FIG. 4, which illustrates the imaging system S of FIGS. 1-3 in a particular position of use, during a biplane radiography, the first machine I on the floor can be moved to the vicinity of one of the longitudinal edges of the table 10 while the tube 2 and the detector 4 are positioned to face an area of interest, in order to free up the frontal zone of the examination table 10, at which the head of the patient is situated.

Finally, it can be seen in FIG. 3 that the central processing unit 16 can cause the movement of one or other of the machines I, II into a position of use facing the area of interest and control the movement of the machine I, II that is not in use into a retracted out-of-the-way position, thereby freeing up the space around the examination table 10.

The X-ray tubes 2, 2' and the detectors 4, 4' are supported by robotic arms comprising multiple axes of articulation allowing them to be moved in three dimensions and to be positioned at various angles of incidence around an area of interest to be examined. In order to prevent any risk of collision between the arms 5, 5' of the two machines I, II, the medical imaging system S is furnished with means for measuring the position of the arms 5, 5' and, notably, of the articulation axes. These means are, for example, formed by a certain number of sensors installed in the arms 5, 5' and capable of measuring the angular position of the axes relative to a fixed reference point.

These various sensors are connected to the central processing unit 16 and thus provide the control programs, stored in memory, with information relating to the position of all the arms of the X-ray machines I, II. Therefore, the central processing unit 16 is kept informed at all times of the position of the arms and may allow or forbid a control instruction capable of causing a collision between the arms.

Furthermore, the examination table 10 or, in general, any fixed or mobile obstacle in the examination room, may also be provided with such sensors, the sensors being connected to the central processing unit 16 in order to inform the central processing unit 16 of the position of the examination table 10 relative to the robotic arm. In consequence, the central processing unit 16 may forbid or allow a control instruction that might cause a collision of the X-ray machines I, II with the table 10. Such sensors may be, for example, optical sensors that deliver location information to the processing unit 16.

Embodiments of the present invention, generally relate to a medical imaging system comprising a first X-ray machine and a second X-ray machine each comprising an X-ray tube and an X-ray detector in which the first and second X-ray machines each comprise a mobile automatic device on which the X-ray tube and the detector are mounted in order to control the automatic movement of the first and second machines, making it possible to automatically move the two machines into an out-of-the-way waiting position when they are not in use, to position one of the machines in a working position and to keep the other machine in a waiting position, or else to adjust the isocentre of the two machines without having to move the patient.

When one of the machines can be automatically moved on the floor, certain zones around the examination table can be freed up, by moving this apparatus into another zone, while retaining the positioning of the X-ray tube and of the detector facing an area of interest.

Moreover, by virtue of the coupling of the machines to a common central unit, and by virtue of controlling the X-ray machines via the central processing unit 16 according to their relative position, it is possible to produce images on multiple planes and to automatically move each of the machines according to examination phases, in order to position them in an out-of-the-way waiting position or to bring them to face an area of interest and to do so while preventing any risk of collision.

By virtue of mounting the two X-ray machines on mobile automatic devices, the movement capabilities of the X-ray machines are considerably increased, which allows improved access to the examination table.

What is claimed is:

1. A multiplane medical imaging system comprising:
   a first X-ray machine and a second X-ray machine each comprising an X-ray tube, an X-ray detector, and a mobile device onto which the X ray tube and the X ray detector are mounted, each mobile device configured to control movement of the X ray machine associated therewith, the first X-ray machine being supported by a robot that can be moved freely on a floor of an examination room; and
   a controller configured to control the mobile devices so that movement of the X-ray machines depends on the positions the X-ray machines relative to each other, and retain at least the positions of the X-ray tube and the X-ray detector of the first X-ray machine relative to an area of interest while moving the robot on the floor.

2. The imaging system according to claim 1, wherein the X-ray tubes and the X-ray detectors are mounted on robotic arms articulated about articulation axes, and wherein the imaging system further comprises sensors configured to measure the position of the arms.

3. The imaging system according to claim 2, wherein the arms comprise sensors configured to measure the position of the articulation axes.

4. The imaging system according to claim 1, wherein the controller is further configured to control the mobile devices according to the position of obstacles.

5. The imaging system according to claim 1, wherein the second X-ray machine is supported by a robot that can be moved on rails on the ceiling of the examination room.

6. The imaging system according to claim 1, further comprising a navigation system configured to locate the robot in the examination room.

7. The imaging system according to claim 1, further comprising:
   a support for a patient to be imaged,
   wherein meeting points of X-rays emitted and received by each of the first and the second machines can move along the support without moving the support.

8. The imaging system according to claim 1, wherein the controller is to retain at least the positions of the X-ray tube and the X-ray detector of the first X-ray machine relative to an area of interest at least during radiography while moving the robot on the floor.

9. A method for moving a multiplane medical imaging system, the system comprising a first X-ray machine and a second X-ray machine each comprising an X-ray tube, an X-ray detector, and a mobile device on which the X-ray tube and the X ray detector are mounted, each mobile device configured to control the movement of the X ray machine associated therewith, the method comprising:
   acquiring first information relating to each of the positions of the first and the second X-ray machines relative to each other;

moving a robot supporting the first machine freely on the floor of an examination room;

acquiring second information relating to the position of the robot;

controlling the movement of the mobile devices according to the first information and the second information; and retaining the positions of the X-ray tube and the X-ray detector of the first X-ray machine relative to an area of interest during operation while moving the robot freely on the floor.

10. The method according to claim 9, further comprising acquiring third information relating to the position of obstacles, wherein the movement of the mobile devices is controlled according to the third information.

11. The method according to claim 9, further comprising moving the first and the second X-ray machines to an out-of-the-way waiting position between two image-taking phases.

12. The method according to claim 9, further comprising moving one of the first and the second X-ray machines into an out-of-the-way waiting position when the other of the first and the second X-ray machines acquires a monoplane image.

* * * * *